(12) United States Patent
Lehr et al.

(10) Patent No.: US 8,759,568 B2
(45) Date of Patent: Jun. 24, 2014

(54) PROCESS FOR PREPARING ISOCYANATES

(75) Inventors: Vanessa Simone Lehr, Mannheim (DE); Carsten Knoesche, Niederkirchen (DE); Torsten Mattke, Freinsheim (DE)

(73) Assignee: BASF SE, Ludwigshafen (DE)

( * ) Notice: Subject to any disclaimer, the term of this patent is extended or adjusted under 35 U.S.C. 154(b) by 301 days.

(21) Appl. No.: 13/256,523

(22) PCT Filed: Apr. 7, 2010

(86) PCT No.: PCT/EP2010/054561
§ 371 (c)(1),
(2), (4) Date: Sep. 14, 2011

(87) PCT Pub. No.: WO2010/115908
PCT Pub. Date: Oct. 14, 2010

(65) Prior Publication Data
US 2012/0004445 A1 Jan. 5, 2012

(30) Foreign Application Priority Data
Apr. 8, 2009 (EP) .................................... 09157627

(51) Int. Cl.
*C07C 263/00* (2006.01)

(52) U.S. Cl.
USPC ............ 560/347; 560/330; 560/336; 560/338

(58) Field of Classification Search
None
See application file for complete search history.

(56) References Cited

U.S. PATENT DOCUMENTS

| 4,549,991 | A  | * | 10/1985 | Disteldorf et al. | 560/347 |
| 7,488,842 | B2 | * | 2/2009 | Knoesche et al. | 560/347 |
| 8,168,818 | B2 | * | 5/2012 | Daiss et al. | 560/347 |
| 2004/0068137 | A1 | | 4/2004 | Herold et al. | |
| 2008/0167490 | A1 | * | 7/2008 | Pohl et al. | 560/347 |
| 2010/0056822 | A1 | * | 3/2010 | Daiss et al. | 560/347 |
| 2010/0076218 | A1 | | 3/2010 | Daiss et al. | |

FOREIGN PATENT DOCUMENTS

| DE | 10 2006 05863 | 6/2008 |
| EP | 1 319 655 | 6/2003 |
| EP | 1 403 248 | 3/2004 |
| EP | 1 555 258 | 7/2005 |
| WO | 2007 028715 | 3/2007 |
| WO | 2008 055899 | 5/2008 |
| WO | 2008 055904 | 5/2008 |

OTHER PUBLICATIONS

U.S. Appl. No. 13/434,135, filed Mar. 29, 2012, Lehr, et al.
International Search Report issued Oct. 13, 2010 in PCT/EP10/054561 filed Apr. 7, 2010.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

The invention relates to a process for preparing isocyanates by reacting the corresponding amines with phosgene, optionally in the presence of an inert medium, in which phosgene and amine are first mixed and converted to the isocyanate in a reactor, and in which a reaction gas which comprises isocyanate and hydrogen chloride leaving the reactor is cooled in a quench by adding a liquid quench medium to form a mixture of reaction gas and quench medium as the product stream. The walls of the quench are essentially completely wetted with a liquid.

12 Claims, No Drawings

PROCESS FOR PREPARING ISOCYANATES

CROSS-REFERENCE TO RELATED APPLICATIONS

This application is a National Stage of PCT/EP2010/054561 filed on Apr. 7, 2010. This application is based upon and claims the benefit of priority to European Application No. 09157627.2 filed on Apr. 8, 2009.

BACKGROUND OF THE INVENTION

The invention relates to a process for preparing isocyanates by reacting the corresponding amines with phosgene, optionally in the presence of an inert medium, in which phosgene and amine are first mixed and converted to isocyanate in a reactor. A reaction gas which comprises isocyanate and hydrogen chloride leaving the reactor is cooled in a quench by adding a liquid quench medium to form a mixture of reaction gas and quench medium as the product stream.

The preparation of isocyanates by phosgenating the corresponding amines can in principle be effected by a liquid phase or gas phase phosgenation. Gas phase phosgenation is notable in that a higher selectivity, a lower holdup of toxic phosgene and a reduced amount of energy are required.

In gas phase phosgenation, an amine-containing reactant stream and a phosgene-containing reactant stream, each in the gaseous state, are mixed. The amine and the phosgene react with release of hydrogen chloride (HCl) to give the corresponding isocyanates. The amine-containing reactant stream is generally present in the liquid phase and has to be evaporated and optionally superheated before being mixed with the phosgene-containing stream.

Corresponding processes for preparing isocyanates in the gas phase are described, for example, in EP-A 1 319 655 or EP-A 1 555 258.

In order to prevent further reactions, it is necessary to cool the reaction mixture rapidly after the end of the reaction. To this end, for example, a liquid quench is used. Such a liquid quench is described, for example, in EP-A 1 403 248 or in DE-A 10 2006 058 634. The quench medium which is added for cooling has a temperature which is in the range from 50 to 200° C. The liquid stream sprayed in cools the reaction gas rapidly to temperatures generally between 100 and 200° C. This forms a biphasic mixture with an isocyanate-rich liquid phase and a low-isocyanate gas phase. The two are then sent to a common separating stage or optionally separate separating stages, for example a distillation stage for separation of hydrogen chloride and phosgene on the one hand, and isocyanate on the other hand.

A disadvantage of liquid quench as described, for example, in EP-A 1 403 248 or DE-A 10 2006 058 634 is that wall regions with low liquid wetting can occur within the liquid quench or the liquid film on the wall regions can break up, which leads to the effect that the dropletized condensate does not flow down rapidly enough. Owing to the longer residence time, this results in undesired further reactions and solid deposits on the walls of the liquid quench. This leads to yield losses and has an adverse effect on the run time of the plant.

It is therefore an object of the present invention to provide a process for preparing isocyanates by reacting the corresponding amines with phosgene, in which further reactions and solid deposits are prevented or greatly reduced.

The object is achieved by a process for preparing isocyanates by reacting the corresponding amines with phosgene, optionally in the presence of an inert medium, in which phosgene and amine are first mixed and converted to isocyanate in a reactor, and in which a reaction gas which comprises isocyanate and hydrogen chloride leaving the reactor is cooled in a quench by adding a liquid quench medium to form a mixture of reaction gas and quench medium as the product stream, wherein the walls of the quench are essentially completely wetted with a liquid.

The complete wetting of the walls of the quench with a liquid prevents a dropletized condensate which flows down too slowly and thus leads to further reactions and solid deposits from forming on the walls. As a result of the wetting of the walls with a liquid, the reaction mixture which condenses out on the walls is discharged from the quench with the liquid. No solid deposits form on the walls of the quench.

In the context of the present invention, "essentially completely wetted" means that all walls of the liquid quench which can come into contact with the reaction mixture are wetted with the liquid. Only the regions of the quench in which no wetting with the reaction mixture is possible need not be wetted.

To prepare the isocyanate, the phosgene and the amine are preferably first fed to a mixing zone in which amine and phosgene are mixed to give a reaction mixture. Subsequently, the reaction mixture is fed to the reactor in which the conversion to the isocyanate is effected. The conversion of amine and phosgene in the reactor preferably proceeds in the gas phase. To this end, the pressure in the reactor is preferably in the range between 0.3 and 3 bar absolute, more preferably in the range from 0.8 to 3.0 bar absolute. The temperature is preferably in the range from 250 to 550° C., especially in the range from 300 to 500° C.

In order to be able to perform the reaction in the gas phase, it is also preferred to add the amine and the phosgene in gaseous form. To this end, the amine preferably has a temperature in the range from 200 to 400° C. The pressure of the amine added is preferably in the range between 0.05 and 3 bar absolute. The temperature of the phosgene added is preferably in the range from 250 to 450° C. To this end, the phosgene is typically heated before addition in the manner known to those skilled in the art.

To heat the phosgene and the amine and to evaporate the amine, for example, electrical heating or direct or indirect heating by combustion of a fuel is used. The fuels used are typically fuel gases, for example natural gas. By virtue of the lowering of the boiling temperature of the amine by lowering the pressure, however, heating is also possible, for example by means of steam. The pressure of the steam is selected here according to the boiling temperature of the amine. A suitable vapor pressure of the steam is, for example, in the range from 40 to 100 bar. This gives rise to a temperature of the steam in the range from 250 to 311° C. However, it is also possible to use steam with a temperature of more than 311° C. to evaporate the amine.

In general, it is necessary to heat the amine to the reaction temperature in a plurality of stages. In general, the amine, for this purpose, is first preheated, then evaporated and then superheated. In general, the evaporation takes the longest residence times and thus leads to decomposition of the amine. In order to minimize this, evaporation at lower temperatures, as arises, for example, through the lower pressure, is advantageous. In order to superheat the evaporated amine to reaction temperature after the evaporation, heating with steam is generally insufficient. For superheating, electrical heating or direct or indirect heating by combustion of a fuel is therefore typically used.

In contrast to the evaporation of the amine, the phosgene is evaporated generally at significantly lower temperatures. For this reason, the phosgene can generally be evaporated using steam. However, the necessary superheating of the phosgene to heat it to reaction temperature is generally also possible only by electrical heating or direct or indirect heating by combustion of a fuel.

The reactor which is used for phosgenation of the amine to prepare isocyanates is known to those skilled in the art. In general, the reactors used are tubular reactors. In the reactor, the amine is reacted with the phosgene to give the corresponding isocyanate and hydrogen chloride. Typically, the phosgene is added in excess, such that the reaction gas which forms in the reactor, as well as the isocyanate formed and the hydrogen chloride, also comprises phosgene.

In addition to the use of a tubular reactor, it is also possible to use essentially cuboidal reaction chambers, for example plate reactors. Any desired different cross section of the reactor is also possible.

Amines which can be used to prepare isocyanates are monoamines, diamines, triamines or higher-functionality amines. Preference is given to using monoamines or diamines. According to the amine used, the corresponding monoisocyanates, diisocyanates, triisocyanates or higher-functionality isocyanates are obtained. Preference is given to preparing monoisocyanates or diisocyanates by the process according to the invention.

Amines and isocyanates may be aliphatic, cycloaliphatic or aromatic. The amines are preferably aliphatic or cycloaliphatic, more preferably aliphatic.

Cycloaliphatic isocyanates are those which comprise at least one cycloaliphatic ring system.

Aliphatic isocyanates are those which have exclusively isocyanate groups bonded to straight or branched chains.

Aromatic isocyanates are those which have at least one isocyanate group bonded to at least one aromatic ring system.

The term "(cyclo)aliphatic isocyanates" is used hereinafter for cycloaliphatic and/or aliphatic isocyanates.

Examples of aromatic mono- and diisocyanates are preferably those having 6 to 20 carbon atoms, for example phenyl isocyanate, monomeric 2,4'- and/or 4,4'-methylene-di(phenyl isocyanate) (MDI), 2,4- and/or 2,6-tolylene diisocyanate (TDI) and 1,5- or 1,8-naphthyl diisocyanate (NDI).

Examples of (cyclo)aliphatic diisocyanates are aliphatic diisocyanates such as 1,4-tetramethylene diisocyanate, 1,6-hexamethylene diisocyanate (1,6-diisocyanato-hexane), 1,8-octamethylene diisocyanate, 1,10-decamethylene diisocyanate, 1,12-dodecamethylene diisocyanate, 1,14-tetradecamethylene diisocyanate, 1,5-diisocyanatopentane, neopentane diisocyanate, 2-methyl-1,5-diisocyanatopentane, derivatives of lysine diisocyanate, tetramethylxylylene diisocyanate (TMXDI), trimethylhexane diisocyanate or tetramethylhexane diisocyanate, and 3(or 4), 8(or 9)-bis(isocyanatomethyl)tricyclo-[5.2.1.0$^{2,6}$]decane isomer mixtures, and cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanato-methyl)cyclohexane, 2,4- or 2,6-diisocyanato-1-methylcyclohexane.

Preferred (cyclo)aliphatic diisocyanates are 1,6-diisocyanatohexane, 1-isocyanato-3,3,5-trimethyl-5-(isocyanatomethyl)cyclohexane and 4,4'-di(isocyanatocyclohexyl)-methane. Particular preference is given to 1,6-diisocyanatohexane, 1,5-diisocyanato-pentane, 1-isocyanato-3,3,5-trimethyl-5-(isocyanatomethyl)cyclohexane and 4,4'-di(isocyanatocyclohexyl)methane.

Amines which are used in the process according to the invention for reaction to give the corresponding isocyanates are those in which the amine, the corresponding intermediates and the corresponding isocyanates are present in gaseous form under the selected reaction conditions. Preference is given to amines which decompose over the duration of the reaction under the reaction conditions to an extent of at most 2 mol %, more preferably to an extent of at most 1 mol % and most preferably to an extent of at most 0.5 mol %. Particularly suitable amines here are especially diamines based on aliphatic or cycloaliphatic hydrocarbons having 2 to 18 carbon atoms. Examples thereof are 1,6-diaminohexane, 1,5-diaminopentane, 1,3-bis(amino-methyl)cyclohexane, 1-amino-3,3,5-trimethyl-5-aminomethylcyclohexane (IPDA) and 4,4-diaminodicyclohexylmethane. Preference is given to using 1,6-diaminohexane (HDA).

For the process according to the invention, it is likewise possible to use aromatic amines which can be converted to the gas phase without significant decomposition.

Examples of preferred aromatic amines are tolylenediamine (TDA), as the 2,4 or 2,6 isomer or as a mixture thereof, for example as an 80:20 to 65:35 (mol/mol) mixture, diaminobenzene, 2,6-xylidine, naphthyldiamine (NDA) and 2,4'- or 4,4'-methylene(diphenyldiamine) (MDA) or isomer mixtures thereof. Among these preference is given to the diamines, particular preference to 2,4- and/or 2,6-TDA or 2,4'- and/or 4,4'-MDA.

To prepare monoisocyanates, it is likewise possible to use aliphatic, cycloaliphatic or aromatic amines, typically monoamines. A preferred aromatic monoamine is especially aniline.

In the gas phase phosgenation, it is desirable that the compounds which occur in the course of the reaction, i.e. reactants (amine and phosgene), intermediates (especially the mono- and dicarbamoyl chlorides which form as intermediates), end products (diisocyanate), and any inert compounds metered in, remain in the gas phase under the reaction conditions. Should these or other components be deposited from the gas phase, for example on the reactor wall or other apparatus components, these deposits can undesirably alter the heat transfer or the flow through the components affected. This is especially true of occurrence of the amine hydrochlorides which form from free amino groups and hydrogen chloride, since the resulting amine hydrochlorides precipitate readily and are re-evaporable only with difficulty.

In order to prevent the formation of by-products, it is preferred to supply phosgene in excess. In order to supply only the proportion of amines needed for the reaction, it is possible to mix the amine with an inert gas. The proportion of inert gas in the amine can be used to adjust the amount of the amine supplied for a given geometry of the feed orifices for the amine and the phosgene. Inert media which can be added are those which are present in gaseous form in the reaction chamber and do not react with the compounds which occur in the course of the reaction. The inert media used may, for example, be nitrogen, noble gases such as helium or argon, aromatics such as chlorobenzene, o-dichlorobenzene, trichlorobenzene, toluene, xylene, chloro-naphthalene, decahydronaphthalene, carbon dioxide or carbon monoxide. Preference is given, however, to using nitrogen and/or chlorobenzene as the inert medium.

Alternatively, it is, however, also possible, for example, in order to avoid too great an excess of phosgene, to add the inert medium to the phosgene.

In general, the inert medium is added in an amount such that the ratio of the gas volumes of inert medium to amine or to phosgene is less than 0.0001 to 30, preferably less than 0.01 to 15 and more preferably less than 0.1 to 5.

In order to reduce or to prevent the formation of undesired by-products, and also to suppress decomposition of the isocyanate formed, the reaction gas is cooled in a quench immediately after the reaction. To this end, a preferably liquid quench medium is added. As a result of evaporation of the quench medium, it absorbs heat and leads to rapid cooling of the reaction gas.

According to the invention, the quench medium comprises a portion of the product stream cooled in the quench. This comprises solvent used for cooling and isocyanate formed in the reaction.

In order to prevent deposits from forming in pipelines, regulating devices and other apparatus parts, especially in the atomizer nozzles of the quench, any solid particles present in the quench medium are removed before addition to the quench.

In order to wet the walls of the quench with a liquid, in a first embodiment, the liquid with which the walls are wetted is sprayed onto the wall with nozzles. Alternatively, it is also possible to feed in the liquid with which the walls are wetted, for example, via an overflow or any other feeds, for example holes or slots.

When the liquid with which the walls are wetted is sprayed onto the walls with nozzles, the liquid can be sprayed into the quench from the top and/or from the bottom.

When the liquid, for example, is sprayed into the quench from the top, the liquid sprayed in has a velocity component in flow direction of the reaction gas and a velocity component at right angles to the flow direction of the reaction gas. In the case that the liquid is sprayed in from the bottom, the liquid sprayed into the quench, with which the walls are wetted, has a velocity component at right angles to the flow direction of the reaction gas and a velocity component counter to the flow direction of the reaction gas.

In order to be able to completely wet the walls of the quench with a liquid, the amount of the liquid sprayed in is such that only a portion of the liquid evaporates in the quench and a sufficiently large portion to achieve complete wetting of the walls does not evaporate.

When the liquid is sprayed onto the wall via nozzles, it is possible to use the same nozzles to spray in both the liquid with which the walls are wetted and the quench medium. The liquid with which the walls are wetted and the quench medium can be sprayed into the quench as a mixture via the same nozzles. It is also possible, however, for example, to use two-substance nozzles, through which firstly the liquid with which the walls are wetted and secondly the quench medium are sprayed in. When the quench medium and the liquid with which the walls are wetted are sprayed in via the same nozzles or via two-substance nozzles, they are preferably sprayed in from the top. However, preference is given to spraying in the quench medium and the liquid with which the walls are wetted via different nozzles.

In addition, it is also possible to spray in the liquid with which the walls are wetted into the quench both from the top and from the bottom. In this case, it is possible, for example, via the nozzles which spray in the liquid from the top, simultaneously also to spray in the quench medium, and, via the nozzles which spray in the liquid from the bottom, the liquid with which the walls are wetted. However, it is also possible here to additionally spray in the quench medium via the nozzles which spray in the liquid from the bottom.

The quench medium and the liquid with which the walls are wetted can also be sprayed in from different directions. The quench medium and the liquid with which the walls are wetted can be sprayed in with the flow direction of the reaction gas, counter to the flow direction of the reaction gas or at any angle with respect to the flow direction of the reaction gas.

Homogeneous liquid wetting and sufficient film thickness of the liquid on the walls can be promoted by suitable surface structuring for accumulation of liquid on the walls.

In a further, alternative embodiment, the walls to be wetted have a porous configuration and the liquid with which the walls are wetted is forced through the pores of the wall. The liquid is forced through the pores, for example, from an external reservoir vessel at higher pressure. It is also possible to configure the wall as an outer jacket and to force the liquid through the outer jacket through the pores in the wall. Forcing the liquid in through the porous wall achieves the effect that the wall is wetted essentially completely with the liquid. The forcing-in of the liquid through the porous wall may be an alternative or an addition to the addition of the liquid via nozzles, an overflow or other feeds.

The liquid with which the walls are wetted comprises, in one embodiment, at least one low boiler and/or at least one relatively high-boiling liquid, a relatively high-boiling liquid being understood to mean any liquid which can be used to wet the wall and does not evaporate completely.

When the liquid comprises a low boiler, it is preferred when the low boiler and the quench medium are the same liquid. More particularly, it is preferred when the low boiler and the quench medium comprise an isocyanate and/or at least one solvent.

When different liquids are used as low boiler and quench medium, it is possible, for example, to use a solvent as the low boiler, and a liquid which comprises an isocyanate and optionally at least one solvent as the quench medium.

When the low boiler and/or the quench medium comprise(s) an isocyanate, it is also preferred when the isocyanate present in the low boiler or in the quench medium is the same as the isocyanate prepared in the reaction. When an isocyanate is present in the low boiler and/or in the quench medium, it is especially preferred when the isocyanate formed in the reaction is first cooled in the quench and in any downstream cooling stages and, after the cooling, a substream is used as the liquid which wets the walls or as the quench medium.

It is also possible to use, as the liquid which wets the walls or as the low boiler, a portion of the substance mixture leaving the quench. This may comprise, as well as the isocyanate, additionally any solvent used and possibly residues of phosgene and hydrogen chloride.

When a quench medium other than the liquid which wets the walls is used, or the quench medium and the liquid with which the walls are wetted are fed in via different addition points, it is preferred when the quench medium is added in liquid form in order to achieve rapid cooling of the reaction gas in the quench. The temperature of the quench medium is preferably in the range from 0 to 250° C., especially in the range from 20 to 220° C. The introduction of the quench medium into the hot reaction gas heats and/or evaporates the quench medium. The heat needed for the heating and the evaporation of the quench medium is drawn from the reaction gas, and the reaction gas is cooled in this way. The temperature to which the reaction gas is cooled can be adjusted, for example, through the amount and the temperature of the quench medium added.

In order to set the temperature with which the quench medium is added to the quench if necessary, the quench medium is preferably passed through a heat exchanger. According to the inlet temperature of the quench medium in the heat exchanger, the quench medium can be heated or cooled therein. Cooling is required, for example, when a portion of the product stream which is used as the quench medium is withdrawn directly downstream of the quench. Heating may arise, for example, when the portion of the product stream which is used as the quench medium is withdrawn at the end of the processing zone and has a temperature lower than the desired temperature with which the quench medium is to be added to the quench. In general, however, it will be necessary to cool the quench medium before addition to the quench.

The temperature with which the liquid with which the walls are wetted is added is likewise preferably in the range from 0 to 250° C., especially in the range from 20 to 220° C. When the liquid with which the walls are wetted comprises a portion of the reaction mixture, it is treated in the same way as the portion of the reaction mixture used as the quench medium. For example, initial heating or cooling to the intended use temperature is possible here too.

When the quench medium and/or the liquid with which the walls are wetted comprises solvent, it is preferred to add solvent to the quench medium or to the liquid with which the walls are wetted before addition to the quench. This allows solvent losses in the liquid with which the walls are wetted or in the quench medium to be balanced out. Suitable solvents which are present in the quench medium or in the liquid with which the walls are wetted are, for example, optionally halogen-substituted hydrocarbons.

The solvent which is present in the quench medium or in the liquid with which the walls are wetted is preferably selected from the group consisting of monochlorobenzene, dichlorobenzene, trichlorobenzene, hexane, benzene, 1,3,5-trimethylbenzene, nitrobenzene, anisole, chlorotoluene, o-dichlorobenzene, diethyl isophthalate, dimethyl isophthalate, tetrahydrofuran, dimethylformamide, xylene, chloronaphthalene, decahydronaphthalene and toluene.

When isocyanate is present in the liquid with which the walls are wetted or in the quench medium, the proportion of isocyanate is in the range from 0 to 100%. For instance, the proportion of isocyanate in the case of a pure low boiler quench is generally 0%. Correspondingly, the proportion of isocyanate in the liquid with which the walls are wetted is likewise 0% when only low boilers are used. In the case of a pure high boiler quench, the proportion of isocyanate is, in contrast, for example, 100%. Alternatively, in a high boiler quench, it is, however, also possible to use a correspondingly high-boiling solvent or solvent mixture which may also comprise isocyanate. The proportion of isocyanate in the liquid with which the walls are wetted may likewise be 100% when it comprises only high boilers. However, in the liquid with which the walls are wetted too, it is also possible for high-boiling solvents or solvent mixtures to be present alternatively or additionally to the isocyanate.

However, isocyanate may also be present in the quench medium in a low boiler quench. The proportion of isocyanate is generally higher in a high boiler quench than in a low boiler quench.

However, both for the quench medium and for the liquid with which the walls are wetted, any desired composition of solvent and isocyanate is possible. The composition depends, for example, also on the point in the process at which the portion of the reaction mixture which is used as the quench medium or as the liquid which wets the walls is branched off.

When the quench medium and the liquid with which the walls are wetted are different liquids, it is possible, for example, that the quench medium comprises low boilers, for example solvents, and the liquid with which the walls are wetted is a higher-boiling substance than the low boiler used as the quench medium, for example pure isocyanate. Preference is given to wetting the walls using relatively high-boiling solvents or solvent mixtures which may also comprise isocyanate.

The high boilers used may, for example, also be the above-mentioned solvents, preferably in a mixture with isocyanate.

In a preferred embodiment, for further treatment, the quench is followed downstream by further stages for cooling the reaction gas. In the individual stages for cooling, the product stream is cooled further in each case until attainment of the desired temperature with which the product stream is sent, for example, to a subsequent workup. The product stream used in the quench is preferably the entire stream leaving the quench, which comprises the quench medium, the reaction mixture and the liquid with which the walls are wetted.

The further stages for cooling which may follow downstream of the quench may, for example, be further quenches or condensers or any other stages for cooling which are known to those skilled in the art. Preferably, at least one of the stages for cooling the product stream which follows downstream of the quench is a condenser. Suitable condensers are any desired condenser designs known to those skilled in the art. Typically, the condenser used is a heat exchanger through which a cooling medium flows. The coolant used may, for example, be water. In this case, the gas condenses out at least partly on the walls of the condenser. The liquid which thus arises runs down and is collected and is withdrawn from the condenser.

The condensing of the product stream is generally followed by a processing step. For example, it is possible that the condensed mixture is scrubbed in a solvent. The solvents used may, for example, be the same substances which can also be used as the quench medium or as the liquid with which the walls are wetted.

Alternatively to the cooling of the product stream, it is also possible that the product stream, after leaving the quench, is fed to a separating stage. An appropriate separating stage may alternatively, however, also follow the condenser, for example. Preferably, however, the separating stage directly follows the quench. Suitable separating stages are, for example, distillation columns or scrubbers.

When the separating stage is a scrubber, the product stream leaving the quench is preferably—as described above—scrubbed with a solvent. This transfers the isocyanate selectively into the scrubbing solution. The scrubbing is then followed by a separation, preferably by means of rectification.

When the separating stage is a distillation column, the gaseous product stream is fed to the rectification column. The rectification column is preferably operated such that the temperature at the top of the rectification column is lower than the boiling temperature of the product stream. In this way, individual constituents of the product stream condense out selectively in the distillation column and can be withdrawn from the column at the bottom, via the top and optionally via side draws.

When the separating stage is a scrubber, a suitable apparatus is especially a scrubbing tower in which the isocyanate formed is removed from the gaseous product stream by condensation in an inert solvent, while excess phosgene, hydrogen chloride and if appropriate the inert medium pass through the scrubbing tower in gaseous form. The temperature of the inert solvent is preferably kept above the dissolution temperature of the carbamoyl chloride corresponding to the amine in the selected scrubbing medium. Particular preference is given to keeping the temperature of the inert solvent above the melting temperature of the carbamoyl chloride corresponding to the amine.

Suitable scrubbers are any desired scrubbers known to those skilled in the art. For example, it is possible to use stirred vessels or other conventional apparatus, for example columns or mixer-settler apparatus.

After it leaves the quench, the mixture of reaction gas, quench medium and liquid scrubbed and worked up with which the walls are wetted is generally as described, for example, in WO-A 2007/028715.

When a condenser is used for processing of the product stream, it is preferred to withdraw the quench medium or the liquid with which the walls are wetted from the condenser. In the case of processing by rectification, preference is given to removing the solvent used as the quench medium or as the liquid with which the walls are wetted. In this case, the solvent still comprises fractions of isocyanates. The mixture of solvent and isocyanate thus removed is then used as the quench medium or as the liquid with which the walls are wetted.

When a portion of the product stream is used as the quench medium or as the liquid with which the walls are wetted, it is possible to branch off this portion from the product stream, for example, after the cooling. Alternatively, the quench medium or the liquid with which the walls are wetted can also be branched off from any desired stream after a workup which follows the quench.

The invention claimed is:

1. A process for preparing an isocyanate by reacting a corresponding amine with phosgene, optionally in the presence of an inert medium, in which phosgene and amine are first mixed and converted to the isocyanate in a reactor, thereby forming a reaction gas comprising isocyanate and hydrogen chloride, and in which the reaction gas leaving the reactor is cooled in a quench by adding a liquid quench medium to form a mixture of the reaction gas and the quench medium as the product stream, which comprises essentially completely wetting the walls of the quench with a liquid.

2. The process according to claim 1, wherein the liquid with which the walls are wetted is sprayed onto the wall with nozzles.

3. The process according to claim 2, wherein the liquid with which the walls are wetted is sprayed into the quench from the top and/or from the bottom.

4. The process according to claim 2, wherein the liquid with which the walls are wetted and the quench medium are sprayed into the quench as a mixture with the same nozzles.

5. The process according to claim 2, wherein the quench medium and the liquid with which the walls are wetted are sprayed into the quench with two-substance nozzles or different nozzles.

6. The process according to claim 1, wherein the liquid with which the walls are wetted is provided via an overflow or other feeds.

7. The process according to claim 1, wherein the liquid with which the walls are wetted comprises at least one low boiler and/or at least one high boiler.

8. The process according to claim 7, wherein the liquid with which the walls are wetted and the quench medium are the same liquid.

9. The process according to claim 7, wherein the liquid with which the walls are wetted comprises an isocyanate and/or at least one solvent.

10. The process according to claim 7, wherein the isocyanate present in the liquid with which the walls are wetted is the same as the isocyanate prepared in the reaction.

11. The process according to claim 10, wherein the reaction gas is first cooled in the quench and any downstream cooling stages and is condensed to a product stream and, after the cooling, a substream is used as the liquid which wets the walls.

12. The process according to claim 9, wherein the liquid with which the walls are wetted comprises at least one solvent is selected from the group consisting of monochlorobenzene, dichlorobenzene, trichlorobenzene, hexane, benzene, 1,3,5-trimethylbenzene, nitrobenzene, anisole, chlorotoluene, o-dichlorobenzene, diethyl isophthalate, tetrahydrofuran, dimethylformamide, xylene, chloronaphthalene, decahydronaphthalene and toluene.

* * * * *